US009498568B2

(12) United States Patent
Nicoletti

(10) Patent No.: US 9,498,568 B2
(45) Date of Patent: Nov. 22, 2016

(54) SYSTEM FOR PACKAGING CONTAINERS IN A CONTROLLED ENVIRONMENT

(71) Applicant: STEVANATO GROUP INTERNATIONAL A.S., Bratislava (SK)

(72) Inventor: Fabiano Nicoletti, Venezia (IT)

(73) Assignee: STEVANATO GROUP INTERNATIONAL A.S., Bratislava (SK)

( * ) Notice: Subject to any disclaimer, the term of this patent is extended or adjusted under 35 U.S.C. 154(b) by 15 days.

(21) Appl. No.: 14/404,389

(22) PCT Filed: May 28, 2013

(86) PCT No.: PCT/IB2013/054398
§ 371 (c)(1),
(2) Date: Nov. 26, 2014

(87) PCT Pub. No.: WO2013/179219
PCT Pub. Date: Dec. 5, 2013

(65) Prior Publication Data
US 2015/0108124 A1    Apr. 23, 2015

(30) Foreign Application Priority Data
May 31, 2012    (IT) .............................. VI2012A0127

(51) Int. Cl.
*A61M 5/00* (2006.01)
*B65D 5/00* (2006.01)
*B65D 5/12* (2006.01)
*B65D 5/32* (2006.01)
*B65D 5/46* (2006.01)
*B65D 77/04* (2006.01)

(52) U.S. Cl.
CPC ............. *A61M 5/002* (2013.01); *A61M 5/008* (2013.01); *B65D 5/003* (2013.01); *B65D 5/12* (2013.01); *B65D 5/323* (2013.01); *B65D 5/4612* (2013.01); *B65D 77/0433* (2013.01)

(58) Field of Classification Search
CPC .......... B65D 21/0212; B65D 21/0215; B65D 5/6632; Y10S 206/821; Y10S 229/915
USPC ......................................................... 206/509
See application file for complete search history.

(56) References Cited

U.S. PATENT DOCUMENTS 2,484,975 A    10/1949    Van Saun
3,000,496 A     9/1961    Larson
(Continued)

FOREIGN PATENT DOCUMENTS

EP            1125849 A2      8/2001
ES    WO 2011141587 A1 *    11/2011    .............. B65D 9/12
FR            2820405 A1      8/2002

OTHER PUBLICATIONS

International Search Report in corresponding PCT application dated Sep. 26, 2013.

*Primary Examiner* — Shawn M Braden
(74) *Attorney, Agent, or Firm* — Hedman & Costigan, P.C.; James V. Costigan; Kathleen A. Costigan

(57) ABSTRACT

The invention relates to a packaging system (1, 20) of two or more objects or containers (2) in a controlled environment, able to contain a first container (1), equipped with a barrier of sterility, and a casing or package (20), externally coupled to the first container (1) and provided with at least one removable wall (8), so that said container (1) can be accessible from outside and/or can be decoupled from said casing or package (20).

10 Claims, 1 Drawing Sheet

(56) References Cited

U.S. PATENT DOCUMENTS

| | | | |
|---|---|---|---|
| 3,390,810 A | 7/1968 | Schneeweiss | |
| 7,365,268 B2* | 4/2008 | Collins | B65D 7/28 174/17 R |
| 7,909,191 B2* | 3/2011 | Baker | A61B 19/026 220/23.4 |
| 2012/0080426 A1 | 4/2012 | McClure | |
| 2013/0213847 A1* | 8/2013 | Moreau | B65D 5/001 206/509 |

* cited by examiner

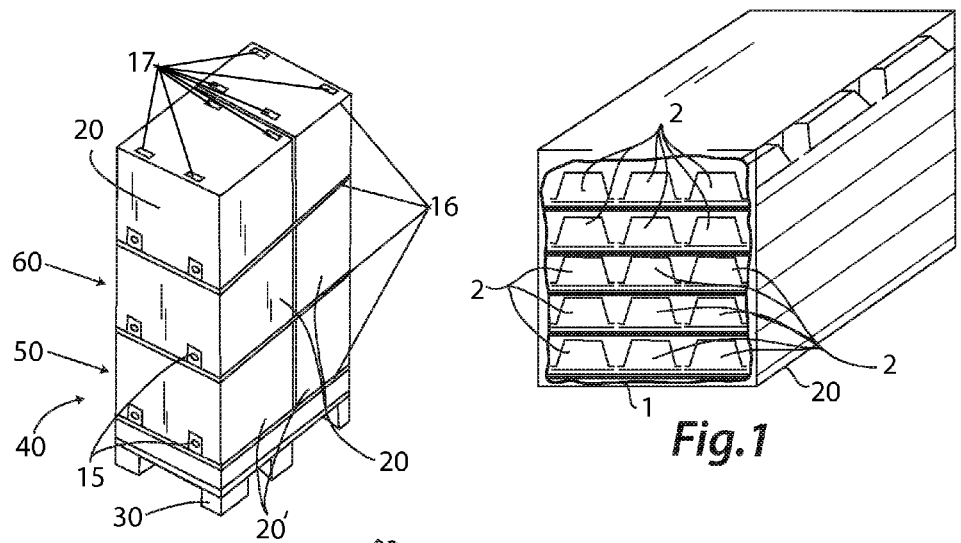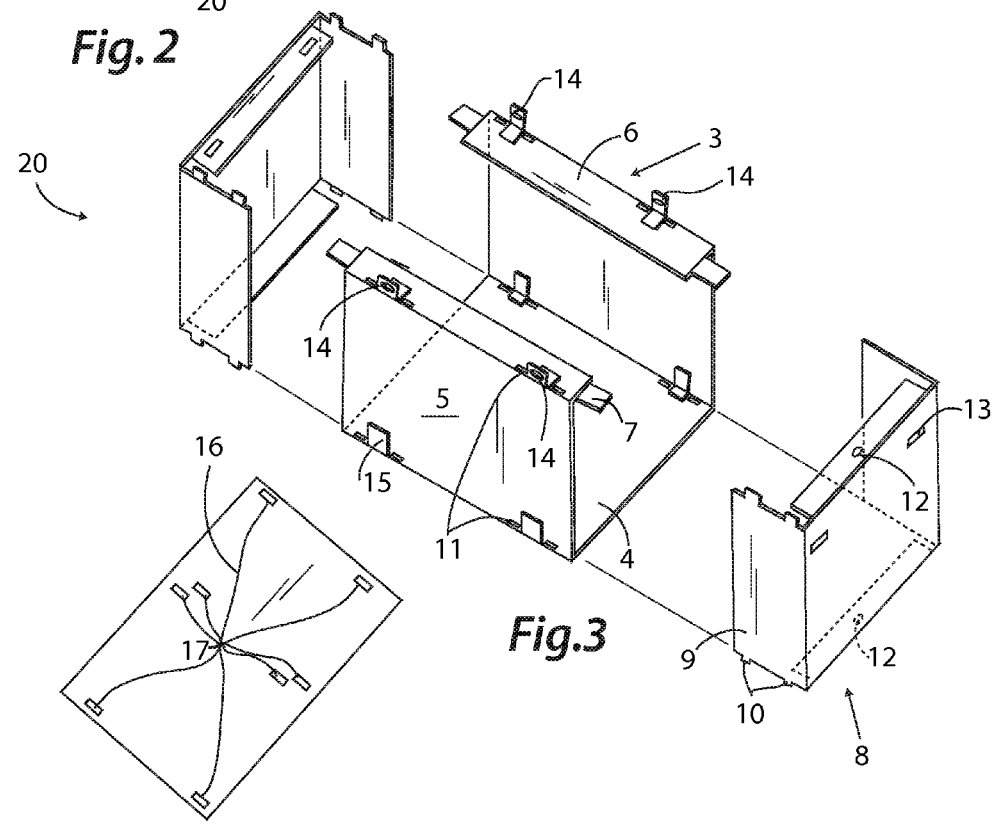

SYSTEM FOR PACKAGING CONTAINERS IN A CONTROLLED ENVIRONMENT

The present invention relates to a system for packaging semi-finished products having some features to be maintained in a controlled and isolated environment—clean, sterile, not toxic, physically or chemically unstable or reactive, etc.—until the time of use or until the time of introduction of the components in the manufacturing process for a next operation.

This packaging is configured to perform the function of isolating the components from outside.

Furthermore, the packaging system must necessarily provide a mechanical and physical resistance so as to maintain the physical integrity of the product during the operations of storage, transport and handling and to facilitate the operations of packing and unpacking without risk of contamination of the components throughout the process.

Depending on the circumstances, this packaging system must allow the execution of special operations such as a sterilization cycle.

More specifically, the invention relates to a system for packaging pharmaceutical containers made of glass, plastic or other materials, which are thus pre-treated, cleaned, sterilized, ready to be filled and closed and which are placed in suitable trays or supports, so that they can be isolated from the outside by one or more sterility barriers, in order to maintain their characteristics during the introduction of the products and without contamination even during the aseptic filling and closing processes.

Sterilized glass syringes, ready to be filled and closed, are well known. Said syringes are usually positioned on a plastic support matrix (the so-called "nest").

The nest is located in a plastic box, sealed with a filtering porous membrane, such as a paper filter or a Tyvek® filter. Said plastic box is protected by a closed container, consisting of a flexible film, which has an opening concealed by a filtering porous membrane or by a Tyvek®. Therefore, the package comprises two superimposed sterility barriers, able to block any contamination, either a bacteriological contamination and/or a contamination due to particles.

It is also possible to add a second container to the first one, so as to form a third sterility barrier.

It is thus possible to place several boxes of the above mentioned type and so isolated inside packages made of corrugated cardboard or plastic, which have sizes and weights suitable to be manually handled during packing and unpacking operations.

Said packages are stacked and positioned on pallets, before being subjected to a final cycle of gas sterilization.

When the packages are used, the products are introduced in the controlled area, for example a sterilized area, by means of an aseptic filling process, which consists of unpacking the units, by opening the package with or without reduced contamination (the operation is performed under an ultra-clean laminar air stream, thus protecting the surface), by removing the box, by performing a biological decontamination of the external surface of the box, commonly with the aid of an e-beam tunnel, and by placing the sterilized box in the aseptic zone.

Finally, it is necessary to remove the Tyvek® filter, so as to use the syringes.

The above mentioned prior art requires the use of a container for each box and sometimes it is also necessary to use a second container; this obviously involves a high cost, both in the production of the products and in their use.

It is therefore an object of the present invention to provide a system for packaging containers in a controlled environment which is simple and which at the same time is able to significantly reduce the amount of packaging material to be used, with respect to the prior art.

Another object of the invention is to provide a system for packaging containers in a controlled environment, which is capable to simplify the handling operations, thereby reducing their costs.

Advantageously, the packaging system of the invention is carried out by means of a sterilized transfer port, which is usually used for inserting small sterilized pieces or components in an aseptic process.

This eliminates any risk of contamination during the introduction of the components in a controlled environment, such as a sterilized environment.

Therefore, it is not necessary to perform a bacteriological decontamination of the surface, thereby significantly reducing the bulk of investment and the high operating costs.

In particular, the packaging system of the invention comprises a container equipped with a barrier of sterility, at least one casing having an internal chamber which houses said container and at least one opening for entering said chamber, and at least one removably wall, which is fixed to the casing and which is able to close said opening, so that the container can be accessed from outside and/or can be extracted from the casing. Preferably, the casing has a central body having a bottom, two side walls, an upper opening and two opposing openings for entering said chamber; advantageously, the two removable partitions are configured to close and open the access openings.

In a preferred embodiment of the invention, the removable wall has teeth that engage in cuts, which are made on the bottom and/or on the walls of the central body.

Furthermore, at least one side wall of said central body has, on its edge opposite to the bottom, a flap, which is parallel to said bottom.

Still according to the invention, the flap has a slot, which is configured to receive gripping means for lifting said structure, in order to advantageously facilitate the loading and unloading of the single casings.

Always according to the invention, the slot is projecting in a direction which is substantially perpendicular to said flap, while the bottom and/or the sides have at least one opening, which is shaped so as to receive said slot.

This advantageously allows to stack more casings one above the other, while maintaining stability.

Additionally, according to the invention, the bottom is substantially flat and the slot and the opening are aligned in a direction which is substantially perpendicular to the bottom.

Furthermore, the invention describes a first layer of said casings and a second layer, superimposed on the first, and a plate, interposed between said first and second layer, to uniformly distribute the weight of the second layer with respect to the first one.

Advantageously, said layers include a single casing or a plurality of casings, depending on their packaging sizes.

In a preferred embodiment of the invention, the plate has at least one through hole, which is shaped to receive said slot.

According to another embodiment of the invention, the plate has at least one first hole, capable to receive each slot of a first casing, and at least one second hole, capable to receive each slot of at least one second casing, so as to mechanically couple side by side said first and second casings.

Still according to the invention, engagement means are provided for mechanically and removably connecting said removable walls and said side walls of the central body.

Advantageously, said engagement means may comprise protrusions, which project from said side walls, and second openings, formed on said removable walls and counter-shaped with respect to said protrusions.

Of course, the position of said protrusions and of the openings can also be reversed.

A further advantage of the present invention is constituted by obtaining a high quality and reliability when sterilized instruments are introduced in a controlled area, for example in a sterilized area.

Further characteristics and advantages of the system for packaging containers and sterilized elements, which is the object of the present invention, will become clear from the following description, relative to preferred embodiments of the invention, and from the enclosed drawings, in which:

FIG. 1 shows an overall view of a packaging included in the packaging system of the invention;

FIG. 2 shows a plurality of packagings of FIG. 1;

FIG. 3 shows an exploded view of the packaging of FIG. 1;

FIG. 4 shows a cover plate for the packaging of FIG. 1.

Referring to the enclosed figures, the system for packaging containers in a controlled environment, which is the object of the present invention, is capable to accumulate, within a large container 1, which is also called "Steribigbag", a plurality of boxes or packagings 2. The container 1 is able to perform the same functions of a known container and therefore it is able to contain a single box or package.

The container 1 is then packaged within a specific casing or package 20 which is designed to achieve high physical resistance features, so as to maintain the integrity of the product during transport, storage, sterilization cycles, etc.

In addition, the package 20 is also designed to facilitate the operations of packing and unpacking products, until the introduction of the package 20 in a controlled environment, such as sterilized environment.

The sizes of the container 1 and the sizes of the relative package 20 may be any, but they are preferably compatible with the useful volume which can be installed on a pallet 30, so that, as shown in FIG. 2, the final volume of the packaging 40 mounted on the pallet 30 is a multiple value of the volume of one package 20.

In particular, the container 1 can have a capacity from 100 to 500 liters, but could also be large up to 1500 liters (by employing a "Euro-pallet" of 1700 mm in height).

The package 20 is made of a conventional corrugated cardboard or of a plastic material and includes:

a "U"-section central body 3 with a bottom 4, two sides 5 and two fins or flaps 6, which laterally terminate in two closing flaps 7, and two closing ends 8, whose side faces 9 have teeth 10 which engage in the cuts 11 made on the bottom 4 and on the fins 6 of the central body 3.

The closing ends 8 have also reinforcements 12 so as to strengthen the package 20 and avoid deformations.

Preferably, the closing ends 8 have also slots 13, which are capable to receive the closing flaps 7 and to lock the fins 6.

Two handles 14 are formed in the fins 6 of the central body 3, so that the hooks of a gripping device can be inserted in the handles 14 to facilitate the gripping of the package 20. In fact, the packages 20 may have a weight up to 50/70 kilos and therefore it can be difficult to handle them without using a handle.

The handles 14 are placed asymmetrically with respect to a longitudinal axis, so that, when several packages 20 are placed side by side, the hooks of a gripping device are able to engage exclusively with the handles 14 of a prefixed package.

In fact, if the handles 14 were symmetrically arranged, they would be very close to the handles 14 of an adjoining package 20 and the hook of the gripping device would undertake both handles 14 belonging to the related packages 20.

In particular, it is possible to add 4 or more handles on the sides of the sheath and they are preferably staggered with respect to the longitudinal axis of the package 20.

Several shaped slots 15 are also formed in the lower part of the sides 5 of the central body 3 and in the bottom 4, so as to receive the handles 14 of a further package 20' on which the package 20 can be stacked.

It is thus possible to interlock a lower package 20' with an upper package 20, in order to increase the stiffness and stability of a pallet formed by a plurality of said stacked packages 20, 20'.

When said packages 20, 20' are positioned on a pallet 30, a plastic corrugated plate 16 is interposed between a first upper layer 50 of packages 20 and a second lower layer 60 of packages 20'. Said plate 16 has through holes 17 in a position corresponding to the position of the handles 14 of the packages 20' of the lower layer 60, so as to insert said handles 14 through the holes 17.

According to the embodiment shown in the enclosed figures, the layers 50 and 60, which are covered by a single plate 16, comprise two packages 20, 20', but it is clear that said layers may have different sizes and may also comprise three or more packages 20, 20'.

Advantageously, the stability of the packaging 40 positioned which is placed on the pallet 30 is thus increased.

In fact, said plates 16 improve the weight distribution of the packages 20 over the whole surface of the lower layers 50 of the packages 20'.

In particular, the use of the packaging system of the invention is the following.

The packing operation involves the step of placing the container 1 in the central body 3 of the package 20 and on a rigid support.

The boxes 2 are placed in the container 1 through the open ends of the central body 3. Since, in fact, said ends of the central body 3 are opened, the container 1 can be easily filled and subsequently closed by welding and also disposed in the package 20.

Then, the closing ends 8 are placed and linked to the central body 3, while the flaps 6 are lowered and fit into the slots 13.

The packages 20 can be handled with the help of grasping means which are attachable to the handles 14, so that said packages 20 can be arranged on a pallet.

At this stage, a final sterilization can take place, as well as during a known packaging method.

Alternatively, it is also possible to perform a treatment in a steam autoclave to the container 1, by placing the container 1 on a metal support and, once full and closed by welding, by subjecting it to a sterilization cycle.

After cooling, the container 1 can be inserted in the central body 3 of the package 20. Then, it is possible to perform the packaging process in a traditional way, as already explained in the above paragraphs.

Regarding the extraction of the objects contained in the packages 20, said packages 20 are unpacked from the pallet 30 with the aid of gripping means attachable to the handles 14 and then they are guided to a supply line.

Moreover, it is possible to provide for a sterilized transfer port in the container 1, which is placed so as to be connected to a corresponding door provided on a wall of an isolator.

The fins 6 are unlocked and one of the closing ends 8 of the package 20 is removed.

The container 1 is coupled, by means of its end provided with the sterilized transfer door, with the corresponding door which is fixed on the wall of the isolator, and by means of said coupling it is thus possible to transfer the boxes 2 directly into the controlled area, for example into the sterilized area.

The boxes 2 may then easily be manually moved in a mechanical way or by means of the upper portion of the flexible film applied to the container 1.

In particular, it is very easy to extract all the boxes 2 if the fins 6 are quite narrow, so that an operator can insert an arm and act below them.

The boxes 2 are therefore transferred into the working area through the sterilized transfer port when said door is open, by passing from a controlled environment, for example from a sterilized environment (the container 1), to another controlled environment (the working area), without coming into contact with any contaminants.

From the above description the technical features of the system for packaging containers in a controlled environment, which is the object of the present invention, are clear as well as the related advantages.

Finally, it is also clear that other embodiments may be provided, without departing from the principles of novelty inherent in the inventive idea as claimed in the appended claims, as it is clear that in the practical implementation of the invention, the materials, shapes and dimensions of the technical details can be any, depending on the requirements, and they can be replaced with other materials, shapes and dimensions which are technically equivalent.

The invention claimed is:

1. System for packaging two or more objects or containers (2) in a controlled environment, suitable for containing a first container (1) provided with a barrier of sterility, characterized in comprising
at least one first package (20) having an internal chamber suitable for housing said first container (1) and at least an access opening to said chamber, and
at least one removable wall (8), suitable for being fixed to, or removed from, said first package (20), respectively in order to close or open said opening, so that said first container (1) can be accessed from outside and/or extracted from said first package (20) said first package (20) having a central body (3) with a bottom (4), two side walls (5), an upper opening and two opposed access openings to said chamber, said system comprising two of said removable walls (8), suitable to close said access openings,
characterized in that at least one of said two side walls (5) of said central body (3) has, on its opposite edge to said bottom (4), a flap (6), which is parallel to said bottom (4) and
in that said flap (6) has a handle (14) which is suitable for receiving gripping means for lifting said first package (20) wherein a first layer (50) of said first package (20) and a second layer (60) of said first package (20), superimposed on said first layer (50), and in comprising a plate (16), interposed between said first layer (50) and said second layer (60), in order to distribute the weight of said second layer (60) in a substantially uniform way over said first layer (50) said plate (16) has at least one through hole (17), which is shaped so as to receive said handle (14) and said plate (16) has at least one first hole (17), suitable for receiving each handle (14) of a first package (20), and at least one second hole (17'), suitable for receiving each handle (14) of at least one second package (20'), for mechanically coupling said first package (20) and said second package (20'), which are placed side by side.

2. System for packaging according to claim 1, characterized in that said handle (14) is projecting substantially perpendicularly with respect to said flap (6), said bottom (4) and/or said sides (5) having at least one first opening (15), which is shaped so as to receive said handle (14).

3. System for packaging according to claim 2, characterized in that said bottom (4) is substantially flat, said handle (14) and said first opening (15) being aligned in a direction substantially perpendicular to said bottom (4).

4. System for packaging according to claim 1, characterized in comprising a closing flap (7) and a slot (13) for mechanically connecting in a removable manner said removable walls (8) and said side walls (5) of said central body (3).

5. System for packaging according to claim 4, characterized in that said engagement means comprise a closing flap (7) projecting from said side walls (5) and a slot (13), formed on said removable walls (8) and shaped corresponding to said closing flap (7).

6. System for packaging characterized in comprising a first layer (50) of said second package (20') and a second layer (60) of said first package (20), superimposed on said first layer (50), and in comprising a plate (16), interposed between said first layer (50) and said second layer (60), in order to distribute the weight of said second layer (60) in a uniform way over said first layer (50).

7. System for packaging according to claim 3, characterized in comprising a first layer (50) of said second package (20') and a second layer (60) of said first package (20), superimposed on said first layer (50) of said second package (20'), and in comprising a plate (16), interposed between said first layer (50) of said second package (20') and said second layer (60) of said first package (60), in order to distribute the weight of said second layer (60) of said first package in a uniform way over said first layer (50).

8. System for packaging according to claim 1, characterized in that said plate (16) has at least one first hole (17), suitable for receiving each handle (14) of a first package (20), and at least one second hole (17'), suitable for receiving each handle (14) of at least one second package (20'), for mechanically coupling said first package (20) and said second package (20'), which are placed side by side.

9. System for packaging according to claim 2, characterized in comprising a closing flap (7) and a slot (13) for mechanically connecting in a removable manner said removable walls (8) and said side walls (5) of said central body (3).

10. System for packaging according to claim 1, characterized in comprising a closing flap (7) and a slot (13) for mechanically connecting in a removable manner said removable walls (8) and said side walls (5) of said central body (3).

* * * * *